(12) United States Patent
Danilov

(10) Patent No.: US 9,133,222 B2
(45) Date of Patent: Sep. 15, 2015

(54) METHOD FOR PRODUCING POLYPRENYL PHOSPHATES

(75) Inventor: Leonid Leonidovich Danilov, Moscow (RU)

(73) Assignee: OBSCHESTVO S OGRANICHENNOY OTVETSTVENNOSTYU GAMAVETFARM ( OOO GAMAVETFARM, Moscow (RU)

( * ) Notice: Subject to any disclaimer, the term of this patent is extended or adjusted under 35 U.S.C. 154(b) by 0 days.

(21) Appl. No.: 13/982,977

(22) PCT Filed: Dec. 28, 2011

(86) PCT No.: PCT/RU2011/001034
§ 371 (c)(1),
(2), (4) Date: Jul. 31, 2013

(87) PCT Pub. No.: WO2012/108786
PCT Pub. Date: Aug. 16, 2012

(65) Prior Publication Data
US 2013/0310606 A1    Nov. 21, 2013

(30) Foreign Application Priority Data

Feb. 4, 2011   (RU) ................................ 2011103976

(51) Int. Cl.
*C08J 11/08* (2006.01)
*C07F 9/06* (2006.01)
*C07F 9/113* (2006.01)

(52) U.S. Cl.
CPC .. *C07F 9/06* (2013.01); *C07F 9/113* (2013.01)

(58) Field of Classification Search
USPC ................................ 568/14; 521/41, 41.5, 42
See application file for complete search history.

(56) References Cited

PUBLICATIONS

Nagano; Bulletin of the Chemical Society of Japan; 69, 2071-2078 (1996).*

* cited by examiner

*Primary Examiner* — Sudhakar Katakam
*Assistant Examiner* — Pancham Bakshi
(74) *Attorney, Agent, or Firm* — Notaro, Michalos & Zaccaria P.C.

(57) ABSTRACT

Method produces polyprenyl phosphates of formula,

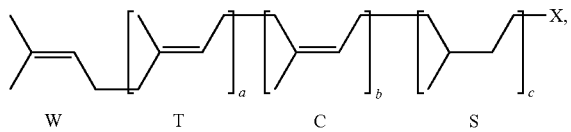

where each isoprene unit contains 5 carbon atoms, W is ω-end isoprene, T is trans-isoprene, C is cis-isoprene, S is 2,3-dihydroisoprene, a=0-10, b=0-39, c=0-1, a+b+c=4-40, and X is of formula $OPO_3MM'$, wherein M and M' are identical or different and are a hydrogen cation or monovalent inorganic or organic cation, or M and M' together are divalent inorganic or organic cation, the phosphorylation of the relevant polyprenol or a mixture of oligomer homologues, where X is hydroxyl group, using a substituted ammonium salt of phosphoric acid in presence of condensing agent, is carried out in a medium of first aprotic organic solvent; and a polyprenyl phosphate of mono- or disubstituted salts thereof with monovalent cations or in form of salts thereof with divalent cations is isolated by extraction and precipitation.

19 Claims, No Drawings

METHOD FOR PRODUCING POLYPRENYL PHOSPHATES

FIELD OF THE INVENTION

The present invention relates to organic chemistry, more particularly to isoprenoid chemistry.

BACKGROUND OF THE INVENTION

Polyprenyl phosphates are lipid-soluble vitamine-like substances which control (directly or indirectly) many physiological processes in all living organisms, from bacteria to human beings (see for example review Swiezewska E. and Danikiewicz W. Polyisoprenoids: structure, biosynthesis and function.//Progr. Lip. Res., 2005, v. 44, p. 235-258). From chemical point of view, they represent monoesters of phosphoric acid with linear long-chain isoprenoid alcohols—polyprenols belonging to isoprenoid class. In living cells, polyprenols and polyprenyl phosphates exist and function in the form of oligomer homologue families with the predominance of one or two compounds, and they are isolated in such a form from natural objects. Isolating polyprenyl phosphates from the natural sources is unprofitable owing to low content thereof, and complexity high labor intensity of the process. Therefore, the compounds are produced via chemical phosphorylation of plant polyprenols as a most available renewable raw material.

Polyprenyl phosphates are irreplaceable coenzymes of glycosyltransferases which participate in biosynthesis of carbohydrate-containing cell biopolymers; their content in biomembranes controls the rate of that process. Chemically synthesized polyprenyl phosphates were used and are used for elucidating in vitro mechanism of action of these compounds within living cells, mainly in regularities of their interaction with glycosyltransferase preparations isolated from the cells (see for example review Danilov L. L. and Druzhinina T. N. Chemical synthesis of dolichyl phosphates, their analogues and derivatives and application of these compounds in biochemical assays.//Acta Biochim Polon., 2007, v. 54, No 4, p. 695-701).

Recently, polyprenyl phosphates began to use for identifying cloned glycosyltransferases, which substrates those polyprenyl phosphates are, and for developing model biochemical in vitro test-systems which are useful for search new efficient antibiotics inhibiting those enzymes and blocking by a new principle a growth and propagation of pathogenic microorganisms which became resistant to existing pharmaceuticals (Borman S. Drug design: first glimpses of cell-wall-forming enzyme will aid search for new antibiotics.//Chem. Eng. News, 2007, March 12, p. 9).

From 80-th years of XX century the investigation of physiological action of exogenic (introduced from outside) polyprenyl phosphates was started and their physiological activity was demonstrated (EP 0149847, 1984, and EP 0165436, 1985). However, owing to unmanufacturability of methods for producing thereof, commercial drugs based on polyprenyl phosphates had not been created.

In 90-th years of XX century in Russian Federation, the remedy for prophylaxis and treatment of infectious diseases and correction of pathological conditions of living organism, the main active ingredients of which are polyprenyl phosphates, had been developed (RU 2129867, 1999, and U.S. Pat. No. 6,525,035, 2003).

For successful manufacture and realization of such preparations in sufficient amounts, a great value has the method for producing their active ingredients, which method must be simple, manufacturable and profit-proved.

Several methods for phosphorylation of polyprenols, non-universal, technically complicated or resulted in low yields, were described in literature before 1980 (see reviews Danilov L. L. and Shibaev V. N. Phosphopolyprenols and their glycosyl esters: chemical synthesis and biochemical application.// In: Studies in natural products chemistry (Atta-ur-Rahman ed., Elsevier, Amsterdam—Oxford—New York—Tokyo), 1991, v. 8, p. 63-114; Shibaev V. N. and Danilov L. L. Synthesis of intermediates in dolichol pathway of protein glycosylation.//In: Glycopeptides and related compounds: synthesis, analysis and applications (D. C. Large and C. D. Warren eds.), Marcel Dekker Inc., New York—Basel—Hong Kong, 1997, p. 427-504).

The first simple and efficient method of phosphorylation of polyisoprenoid alcohols with $POCl_3$ (Danilov L. L., Chojnacki T. A simple procedure for preparing dolichyl monophosphates by the use of $POCl_3$.//FEBS Lett., 1981, v. 131, p. 310-312) was proved to be applicable only for preparing 2,3-dihydropolyprenyl phosphates (dolichyl phosphates). On the basis of this method with small modifications, a method for producing phosphates of that polyprenol subclass was patented (EP 0149847, 1985; U.S. Pat. No. 4,792,615, 1986, and U.S. Pat. No. 5,306,714, 1994).

In 1988, a simple universal method for producing polyprenyl phosphates (including 2,3-dihydropolyprenyl phosphates) had been developed comprising a step of interacting $C_{15}$-$C_{95}$-polyprenols with substituted ammonium salts of phosphoric acid and trichloroacetonitrile in the medium of aprotic organic solvent at molar ratio polyprenol:phosphoric acid salt:trichloroacetonitrile of 1:(4-10):(25-50) followed by successive steps of treating the reaction product with ammonia, hydrolyzing with aqueous solution of 4-dimethylaminopyridine or N-methylimidazole, and isolating and purifying the target compounds by anion-exchange column chromatography (SU 1432065, 1988, taken as the closest analog, see Comparative Example 16 below). As a result, ammonium salts of polyprenyl phosphates were obtained.

Based at this principle of phosphorylation, similar procedures (with or without hydrolysis) for producing polyprenyl phosphates and their modified derivatives were described later (Danilov L. L., Maltsev S. D., and Shibaev V. N. Phosphorylation of polyprenols by tetra-n-butylammonium phosphate at the presence of trichloroacetonitrile.//Bioorgan. Khim, 1988, v. 14, No 9, p. 1287-1289; Danilov L. L. and Shibaev V. N. Phosphopolyprenols and their glycosyl esters: chemical synthesis and biochemical application.//In: Studies in natural products chemistry (Atta-ur-Rahman ed., Elsevier, Amsterdam—Oxford—New York—Tokyo), 1991, v. 8, p. 63-114).

Recently, a method for producing polyprenyl phosphates based on another principle, the interaction of polyprenols with pyrophosphoric acid in the presence of nitrogen base in the medium of aprotic organic solvent followed by basic hydrolysis of formed in the reaction process of symmetrical diester of pyrophosphoric acid (CN 1709894, 2008). The purification of obtained polyprenyl phosphates was achieved by column chromatography procedures, therefore, this method giving no advantages as compared with above method and its modifications.

The main drawbacks of above analogs are:
1) the non-optimized reagent ratio in carrying out the reaction;
2) in some cases, the necessity of hydrolysis for increasing yield of required compound;

3) the step of isolating and purifying the desired compounds by anion-exchange column chromatography;
4) using expensive import adsorbents such as DEAE-cellulose DE-52;
5) expending bulk of solvents for this purpose;
6) isolating of purified polyprenyl phosphates mainly in the form of ammonium salts unstable in storage and hardly solubilized in aqueous medium (the consequence of using ammonium acetate solutions as eluent at anion-exchange chromatography).

Ammonium salts of polyprenyl phosphates, which are convenient for producing and isolating in laboratory conditions in milligram quantities, were used and are often used up to the present for biochemical assays in cell-free enzymic systems (Danilov L. L. and Druzhinina T. N. Chemical synthesis of dolichyl phosphates, their analogues and derivatives and application of these compounds in biochemical assays.//Acta Biochim Polon., 2007, v. 54, No 4, p. 695-701). However, they are unsuitable for manufacturing medicinal agents in commercial scales and for investigating mechanism of physiological and therapeutic action of polyprenyl phosphates at cell and higher levels up to whole organisms, where pharmaceutically acceptable, stable and solubilizable in aqueous medium salts of polyprenyl phosphates are required. A cation nature and a substitution extent of phosphate group by those cations can substantionally impact on physico-chemical properties of the substances. Moreover, it is known that different cations themselves possess unequal physiological action on an organism.

So, the development of simple, manufacturable and profit-proved method for producing polyprenyl phosphates having a wide spectrum of physiologically accepted cations is important for creating new generation of pharmaceuticals on their basis, as well as for improving methods for biochemical investigations thereof.

SUMMARY OF THE INVENTION

The task of the invention is to develop universal, manufacturable and profit-proved method for producing polyprenyl phosphates.

For solving this task and achieving the mentioned result, the present invention provides a method for producing polyprenyl phosphates having general structural formula:

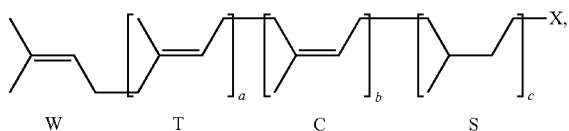

where each isoprene unit contains 5 carbon atoms, W means a ω-end isoprene unit, T means a trans-isoprene unit, C means a cis-isoprene unit, S means a 2,3-dihydroisoprene unit, a=0-10, b=0-39, c=0-1, a+b+c=4-40, and X means a group of the formula $OPO_3MM'$, wherein M and M' are identical or different and are a hydrogen cation or monovalent inorganic or organic cation, or M and M' together are divalent inorganic or organic cation. The claimed method comprises steps of: carrying out a phosphorylation reaction of the corresponding polyprenol or the mixture of oligomer homologues of mentioned formula, where X means hydroxyl group, using substituted ammonium salt of phosphoric acid in the presence of condensing agent in a medium consisting of a first aprotic organic solvent; and isolating, by extraction and precipitation, the polyprenyl phosphate in the form of mono- or disubstituted salts thereof with monovalent cations or in the form of salts thereof with divalent cations.

The special feature of the method according to the present invention consist in that polyprenol molecules can contain at least 5 isoprene units (at least 25 carbon atoms), preferably from 6 to 20 isoprene units (from 30 to 100 carbon atoms).

One more special feature of the method according to the present invention consists in that as substituted ammonium salt of phosphoric acid dihydrophosphates selected from the group consisting of diisopropylethylammonium dihydrophosphate, tetramethylammonium dihydrogen phosphate, tetraethylammonium dihydrogen phosphate, tetrabutylammonium dihydrogen phosphate or cetyltrimethylammonium dihydrogen phosphate, and bis(diisopropylethylammonium) hydrogen phosphate, preferably tetrabutylammonium dihydrogen phosphate, can be used.

One more special feature of the method according to the present invention consists in that trichloroacetonitrile or dicyclohexylcarbodiimide, preferably trichloroacetonitrile, can be used as condensing agent. Herewith, the molar ratio of polyprenol:substituted ammonium salt of phosphoric acid: trichloroacetonitrile can be 1:0.1-10:0.1-10, preferably not far from 1:1:1.

One more special feature of the method according to the present invention consists in that the solvent selected from the group consisting of benzene, toluene, dichloromethane, chloroform or dimethylformamide, or the mixture of one from the solvents with acetonitrile can be used as the first aprotic organic solvent.

The special feature of the method according to the present invention consists also in that the polyprenyl phosphate can be isolated in the form of disubstituted salt thereof with monovalent cation when carrying out steps of: distilling off the first aprotic organic solvent from the reaction mixture or from its part; removing the water-soluble impurities from the obtained residue by extraction in the system the first organic solvent-water; evaporating the organic phase; precipitating the unpurified disubstituted salt of polyprenyl phosphate by treating with solution of the monovalent metal salt and hydroxide of this metal in the alcohol; extracting non-phosphorylated compounds consecutively with the alcohol and second aprotic organic solvent in which the salt of polyprenyl phosphate is insoluble. As a result the disubstituted salt of polyprenyl phosphate having at least 95 wt % purity is obtained.

Herewith, a compound selected from the group consisting of petroleum ether, benzene, toluene, chloroform, dichloromethane, butanol, isoamyl alcohol or mixture thereof can be used as the first organic solvent in the system the first organic solvent-water; a compound selected from the group consisting of methanol, ethanol, propanol, isopropanol or mixture thereof can be employed as the alcohol for extraction; a solution containing from 1 to 10 wt % of compound selected from the group consisting of lithium, sodium or potassium formiate, acetate, chloride, bromide or iodide, and from 0 to 10 wt % of corresponding metal hydroxide, in the alcohol can be utilized; a compound selected from the group consisting of acetonitrile, acetone or mixture thereof can be used as the second aprotic organic solvent.

One more special feature of the method according to the present invention consist in that the polyprenyl phosphate can be isolated in the form of monosubstituted salt thereof with monovalent cation or of salt with divalent cation, when carrying out steps of: distilling off the first aprotic solvent from the reaction mixture or from a part thereof; removing the water-soluble impurities from the obtained residue by treating its solution in second organic solvent with aqueous solution of the salt of ammonium, mono- or divalent metal or organic base with strong acid followed by evaporating the second organic solvent and removing aqueous phase; extracting the non-phosphorylated impurities by solubilizing the obtained waxy residue in third organic solvent and adding the second organic solvent in which the salt of polyprenyl phosphate is insoluble, followed by evaporating the third organic solvent and simultaneously precipitating the desired product; removing a supernatant. As a result the monosubstituted salt of polyprenyl phosphate or its salt with divalet cation having at least 95 wt % purity is obtained.

A compound selected from the group consisting of the alcohol or its mixture with carbon tetrachloride, pentane, hexane, dichloromethane, chloroform or diethyl ether can be used as the second organic solvent; a compound selected from the group consisting of methanol, ethanol, propanol or isopropanol can be employed as the alcohol; a solution containing from 0.5 to 10 wt % of compound composed from nitrate, bromide, chloride, sulfate or hydrogen sulfate anion and monovalent cation selected from the group consisting of lithium, sodium, potassium, ammonium, hydroxyethylammonium, dimethyl hydroxyethyl ammonium, choline, triethylammonium or triethanolammonium, or divalent cation selected from the group consisting of calcium, magnesium, manganese or zinc can be used as the aqueous solution of the salt; a low-boiling compound selected from the group consisting of diethyl ether, dichloromethane, pentane, hexane or mixture thereof can be explored as the third organic solvent; a compound selected from the group consisting of acetonitrile, acetone or the mixture thereof can be used as the second aprotic organic solvent.

DETAILED DESCRIPTION OF THE PREFERRED EMBODIMENTS

The invention, as mentioned above, relates to the method for preparing polyprenyl phosphates (the monoesters formed by phosphoric acid and polyprenols) from corresponding polyprenols. Polyprenols are linear isoprenoid alcohols which consist of at least 5 isoprene units linked "head-to-tail" and contain hydroxyl group as a rule at C1 atom. Polyprenols, including their 2,3-dihydro-derivatives, and corresponding phosphates obtained from those compounds can be represented by the following general formulae:

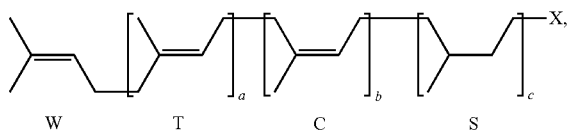

which in abbreviated notation according to IUPAC-IUB recommendations (IUPAC-IUB joint commission on biochemical nomenclature, Prenol nomenclature recommendations.// Eur. J. Biochem., 1987, v. 167, p. 181-184) can be written as follows:

$$WT_aC_bS_c—X,$$

where each isoprene unit contains 5 carbon atoms, W means a ω-isoprene unit, T means a trans-isoprene unit, C means a cis-isoprene unit, S means a 2,3-dihydroisoprene unit, a=0-10, b=0-39, c=0-1, a+b+c=4-40; X means OH (hydroxyl group) for polyprenols, and X means $OPO_3MM'$ for polyprenyl phosphates; M and M' are identical or different and means hydrogen cation or monovalent inorganic or organic cation, or M and M' together means divalent inorganic or organic cation.

Natural sources contain mainly mixtures of polyprenol (and corresponding polyprenyl phosphate) oligomer homologues containing 30-100 carbon atoms (from 6 to 20 isoprene units). The individual polyprenols can be isolated from the natural oligomer homologue mixtures by reversed-phase high-performance liquid chromatography (RP HPLC) and phosphorylated with high efficiency. Practically, all living organisms including human beings produce the oligomer homologue families of polyprenols and polyprenyl phosphates, and individual polyprenyl phosphates possess biological activity similar to that of the natural mixtures, but the cost of individual ones is much higher in comparison with the mixtures, and for that reason the use of the individual polyprenyl phosphates for pharmaceutical production is questionable. Chemical synthesis of polyprenols is multistage, laborious and expensive. Therefore, in the present invention, following initial polyprenols are used as examples, but without limitation, which are named mainly in accordance with an extraction source (digits in bold type indicate numbers of Examples below):

a) pinoprenol 1 (total polyprenols isolated from green parts of coniferous species particularly of pine (*Pinus* species) or fir (*Abies* species) tree, $WT_2C_{10-16}$—OH, designated as $C_{65-95}$-polyprenol containing at the average about 16 isoprene units;

b) 2,3-dihydropinoprenol 2 ($WT_2C_{9-15}S$—OH, designated as $C_{65-95}$-2,3-dihydropolyprenol, which can be synthesized by selective hydrogenation of α-isoprene unit of pinoprenol 1);

c) moraprenol 3 (total polyprenols isolated from leaves of trees particularly of mulberry (*Morus* species), $WT_3C_{5-9}$—OH, designated as $C_{45-65}$-polyprenol containing at the average about 11 isoprene units;

d) betulaprenol 4 (total polyprenols isolated from wood particularly of birch (*Betula* species), $WT_2C_{3-6}$—OH, designated as $C_{30-45}$-polyprenol containing at the average 7 isoprene units.

As the examples of obtained polyprenyl phosphates (in the form of mono- or disubstituted salts with monovalent cations or of salts with divalent cations), the following ones (but without limiting with this list) are selected:

e) disodium pinoprenyl phosphate 5 ($WT_2C_{10-16}$—$OPO_3^{2-}$ $2Na^+$);

f) disodium moraprenyl phosphate 6 ($WT_3C_{5-9}$—$OPO_3^{2-}$ $2Na^+$);

g) sodium pinoprenyl hydrogen phosphate 7 ($WT_2C_{10-16}$—$OPO_3H^-Na^+$);

h) ammonium pinoprenyl hydrogen phosphate 8 ($WT_2C_{10-16}$—$OPO_3H^-NH_4^+$);

i) dimethyl hydroxyethyl ammonium pinoprenyl hydrogen phosphate 9 ($WT_2C_{10-16}$—$OPO_3H^-(CH_3)_2NH^+CH_2CH_2OH$);

j) sodium 2,3-dihydropolyprenyl hydrogen phosphate 10 ($WT_2C_{9-15}S$—$OPO_3H^-Na^+$);

k) sodium moraprenyl hydrogen phosphate 11 ($WT_3C_{5-9}$—$OPO_3H^-Na^+$);

l) ammonium moraprenyl hydrogen phosphate 12 ($WT_3C_{5-9}$—$OPO_3H^-NH_4^+$);

m) magnesium moraprenyl phosphate 13 ($WT_3C_{5-9}$—$OPO_3^{2-}Mg^{2+}$);

n) sodium betulaprenyl hydrogen phosphate 14 ($WT_2C_{3-6}$—$OPO_3H^-NH^+$);

o) ammonium betulaprenyl hedrogen phosphate 15 ($WT_2C_{3-6}$—$OPO_3H^-NH_4^+$).

The method according to the present invention is realized as follows.

At first, the initial polyprenols are phosphorylated with substituted ammonium salt of phosphoric acid and trichloroacetonitrile as condensing agent in the medium of the first aprotic organic solvent.

As the substituted ammonium salt of phosphoric acid, dihydrophosphates can be used selected from the group consisting of diisopropylethylammonium dihydrophosphate, tetramethylammonium dihydrogen phosphate, tetraethylammonium dihydrogen phosphate, tetrabutylammonium dihydrogen phosphate or cetyltrimethylammonium dihydrogen phosphate, and bis(diisopropylethylammonium)hydrogen phosphate, preferably tetrabutylammonium dihydrogen phosphate.

As the condensing agent, dicyclohexylcarbodiimide can be used besides trichloroacetonitrile. The molar ratio of polyprenol, substituted ammonium salt of phosphoric acid and trichloroacetonitrile can be within 1:0.1-10:0.1-10, preferably not far from 1:1:1.

As the first aprotic organic solvent, benzene, toluene, dichloromethane, chloroform or dimethylformamide, or the mixture of one from the solvents with acetonitrile can be used. The reaction can be performed at 0-70° C. during 0.5-72 h.

The mentioned step of isolating polyprenyl phosphates in the form of disubstituted salt thereof with monovalent cation is carried out in the course of the next steps.

The reaction mixture obtained after phosphorylation reaction or a part thereof is evaporated to dryness, and water-soluble impurities are removed by liquid extraction (2-7 times) in a system of first organic solvent-water. As the first organic solvent for the extraction of water-soluble impurities, petroleum ether, benzene, toluene, chloroform, dichloromethane, butanol, isoamyl alcohol or mixture thereof can be used.

Further, the organic phase is evaporated, the residue is dissolved in the alcohol and is treated with a solution of excess of monovalent metal salt in the alcohol possibly containing hydroxide of the metal. Thereat the unpurified disubstituted salt of polyprenyl phosphate precipitates. After the total precipitation is completed, the supernatant is removed and the precipitation is repeated. The residue is extracted with the alcohol (2-7 times) for removing the salt and the metal hydroxide and with the second aprotic solvent (1-5 times) for removing of non-phosphorylated compounds.

As the alcohol, methanol, ethanol, propanol, isopropanol or their mixture can be used.

As the precipitating agent, 1-10 wt % solution of lithium, sodium or potassium formiate, acetate, chloride, bromide or iodide, containing from 0 to 10 wt % of corresponding metal hydroxide, in the alcohol can be utilized.

As the second organic solvent, acetonitrile, acetone or their mixture can be employed.

Waxy residue is dried in vacuum at 20-100° C. and the disubstituted salt of polyprenyl phosphate having at least 95 wt % purity is obtained.

The mentioned step of isolating polyprenyl phosphates in the form of their monosubstituted salt with monovalent cation or of salt with divalent cation is carried out in the course of the next steps.

The reaction mixture obtained after phosphorylation or a part thereof is evaporated to dryness, the residue is dissolved in a second organic solvent and the excess of aqueous solution of the salt of ammonium, mono- or divalent metal or organic base with strong acid is added. As the second organic solvent, an alcohol or its mixture with carbon tetrachloride, pentane, hexane, dichloromethane, chloroform or diethyl ether can be used. As the alcohol, methanol, ethanol, propanol or isopropanol can be employed. An aqueous solution containing from 0.5 to 10 wt % of compound selected from the group consisting of nitrate, bromide, chloride, sulfate or hydrogen sulfate of lithium, sodium, potassium, ammonium, hydroxyethylammonium, dimethyl hydroxyethyl ammonium, choline, triethylammonium or triethanolammonium as monovalent cation, or calcium, magnesium, manganese or zink as divalent cation can be used as the aqueous solution of the salt.

The second organic solvent is distilled off, and aqueous phase is separated from waxy product. The product is redissolved in the second organic solvent, and the excess of aqueous solution of the above mentioned salt is added.

The second organic solvent is evaporated off, and the aqueous phase is separated from waxy product. The operation is repeated 2-5 times, and non-purified waxy polyprenyl phosphate in the form of corresponding monosubstituted salt or divalent metal salt is obtained. The waxy product is dissolved in a third organic solvent, the excess of second aprotic organic solvent is added, and the third organic solvent is distilled off. As the third organic solvent, a low-boiling compound, for example diethyl ether, dichloromethane, pentane, hexane or mixture thereof can be explored; as the second aprotic organic solvent, an acetonitrile, acetone or the mixture thereof can be used.

The transparent supernatant containing non-phosphorylated impurities is removed, and the procedure is repeated 1-3 times. The residue is dried in vacuum at 20-100° C., and the waxy salt of the polyprenyl phosphate having at least 95 wt % purity is obtained.

The feasibility of the method according to the present invention is illustrated by the following examples.

Example 1

Phosphorylation of Pinoprenol (1)

150 g (136 mmol) of pinoprenol (1) and 60 g (177 mmol) of tetrabutylammonium dihydrogen phosphate are dissolved in 700 ml of dichloromethane, 17 ml (170 mmol) of trichliroacetonitrile are added and the volume of the reaction mixture is brought to 1000 ml with dichloromethane. The mixture is agitated and stored 18 h at the room temperature.

Example 2

Phosphorylation of 2,3-dihydropinoprenol (2)

0.110 g (0.10 mmol) of 2,3-dihydropinoprenol (2) and 0.037 g (0.11 mmol) of tetrabutylammonium dihydrogen phosphate are dissolved in 0.8 ml of dichloromethane, 0.011 ml (0.11 mmol) of trichliroacetonitrile are added and the volume of the reaction mixture is brought to 1 ml with dichloromethane. The mixture is agitated and stored 20 h at the room temperature.

Example 3

Phosphorylation of Moraprenol (3)

150 g (196 mmol) of moraprenol (3) and 85 g (254 mmol) of tetrabutylammonium dihydrogen phosphate are dissolved in 1100 ml of dichloromethane, 17 ml (170 mmol) of trichliroacetonitrile are added and the volume of the reaction mixture is brought to 1500 ml with dichloromethane. The mixture is agitated and stored 24 h at the room temperature.

Example 4

Phosphorylation of Betulaprenol (4)

5.31 g (10.6 mmol) of betulaprenol (4) and 4.0 g (12 mmol) of tetrabutylammonium dihydrogen phosphate are dissolved in 40 ml of dichloromethane, 1.4 ml (14 mmol) of trichliroacetonitrile are added and the volume of the reaction mixture is brought to 60 ml with dichloromethane. The mixture is agitated and stored 25 h at the room temperature.

Example 5

Preparation of Disodium Pinoprenyl Phosphate (5)

The final reaction mixture prepared according to example 1 is evaporated to dryness in vacuum. The residue is dissolved in 800 ml of butanol and extracted with 200 ml of distilled water for 4 times. The organic phase is evaporated to dryness in vacuum, the residue is dissolved in 300 ml of ethanol, and the solution of 38 g of sodium acetate and 5 g of sodium hydroxide in 1000 ml of ethanol is added. The mixture is stored at 4° C. to the total transparency of the supernatant. The supernatant is removed, 400 ml of ethanol are added to the residue, the mixture is agitated at 60° C. during 1 h, 500 ml of above mentioned solution of sodium acetate and sodium hydroxide in ethanol are added, and the mixture is stored at 4° C. to the total transparency of the supernatant again. After removing the supernatant, the residue is extracted with 400 ml of ethanol at 60° C. with agitation, and supernatant is removed. The procedure is repeated twice. The residual ethanol is evaporated in vacuum, and the residue is extracted with 500 ml acetone during 2 h at 60° C. with agitation. The mixture is cooled to the room temperature. After the total formation of the precipitate is completed, the supernatant is removed and the procedure is repeated 3 times. The waxy residue is dried in vacuum at 60° C. during 2 h and 144 g (117 mmol, 86%) of disodium pinoprenyl phosphate (5) is obtained.

$^1$H NMR (CDCl$_3$—CD$_3$OD, 5:1): 5.30 (1H, t, J 7.0, HC2=), 5.05 (15H, m, CH=), 4.30 (2H, br. dd, $J_{H,H}$=$J_{H,P}$=6.0, CH$_2$O—), 1.95 (60H, m, CH$_2$—), 1.68 (3H, s, CH$_3$—C3=), 1.60 (39H, m, CH$_3$C=, Z- and W$_Z$-isoprene unit), 1.51 (9H, m, CH$_3$C=, E- and W$_E$-isoprene unit). $^{31}$P NMR (CDCl$_3$—CD$_3$OD, 5:1): 5.4 (s).

Example 6

Preparation of Disodium Moraprenyl Phosphate (6)

The final reaction mixture prepared according to example 3 is evaporated to dryness in vacuum. The residue is dissolved in 1200 ml of butanol and extracted with 300 ml of distilled water for 4 times. The organic phase is evaporated to dryness in vacuum, the residue is dissolved in 400 ml of ethanol, and the solution of 55 g of sodium acetate and 7 g of sodium hydroxide in 1500 ml of ethanol is added. The mixture is stored at 4° C. to the total transparency of the supernatant. The supernatant is removed, 550 ml of ethanol are added to the residue, the mixture is agitated at 60° C. during 1 h, 700 ml of above mentioned solution of sodium acetate and sodium hydroxide in ethanol are added, and the mixture is stored at 4° C. to the total transparency of the supernatant again. After removing the supernatant, the residue is extracted with 550 ml of ethanol at 60° C. with agitation, and supernatant is removed. The procedure is repeated 2 times. The residual ethanol is evaporated in vacuum, and the residue is extracted with 700 ml acetone during 2 h at 60° C. with agitation. The mixture is cooled to the room temperature. After the total formation of the precipitate is completed, the supernatant is removed, and the procedure is repeated 3 times. The waxy residue is dried in vacuum at 60° C. during 2 h and 143 g (161 mmol) of disodium moraprenyl phosphate (6) is obtained; the yield is 82%.

$^1$H NMR (CDCl$_3$—CD$_3$OD, 5:1): 5.30 (1H, t, J 7.0, HC2=), 5.05 (10H, m, CH=), 4.30 (2H, br. dd, $J_{H,H}$=$J_{H,P}$=6.0, CH$_2$O—), 1.95 (40H, m, CH$_2$—), 1.68 (3H, s, CH$_3$—C3=), 1.60 (21H, m, CH$_3$C=, Z- and W$_Z$-isoprene unit), 1.51 (12H, m, CH$_3$C=, E- and W$_E$-isoprene unit). $^{31}$P NMR (CDCl$_3$—CD$_3$OD, 5:1): 5.1, (s).

Example 7

Preparation of Sodium Pinoprenyl Hydrogen Phosphate (7)

From the final reaction mixture (prepared according to example 1) 147 ml containing initially 22 g (20 mmol) of pinoprenol (1) are separated and evaporated to dryness in vacuum. The residue is dissolved in 200 ml of ethanol, 200 ml of 5% aqueous solution of NaCl is added, the mixture is agitated, and ethanol is distilled off in vacuum. After cooling to the room temperature and reaching total transparency of aqueous phase, the latter is removed. The waxy product is dissolved in 100 ml of dichloromethane, 200 ml of ethanol are added under agitation followed by the adding 200 ml of 5% aqueous solution of NaCl, and the organic solvents are distilled off in vacuum. After cooling to the room temperature and reaching total transparency of aqueous phase, the latter is removed. The procedure is repeated 2 times. The residue is washed with 20 ml of distilled water and 20 ml of ethanol and dissolved in 50 ml of dichloromethane. 250 ml of acetone are added to the solution, the mixture is agitated, and dichloromethane is evaporated off. After reaching total transparency of supernatant, it is removed. The residue is dissolved in 50 ml of dichloromethane, and the procedure is repeated. The waxy substance is dried in vacuum at 50-60° C. and 21 g (17 mmol) of sodium pinoprenyl hydrogen phosphate (7) is obtained; the yield is 85%.

$^1$H NMR (CDCl$_3$—CD$_3$OD, 5:1): 5.30 (1H, t, J 7.0, HC2=), 5.05 (15H, m, CH=), 4.30 (2H, br. dd, $J_{H,H}$=$J_{H,P}$=6.0, CH$_2$O—), 1.95 (60H, m, CH$_2$—), 1.68 (3H, s, CH$_3$—C3=), 1.60 (39H, m, CH$_3$C=, Z- and W$_Z$-isoprene unit), 1.51 (9H, m, CH$_3$C=, E- and W$_E$-isoprene unit). $^{31}$P NMR (CDCl$_3$—CD$_3$OD, 5:1): 4.3 (s).

Example 8

Preparation of Ammonium Pinoprenyl Hydrogen Phosphate (8)

From the final reaction mixture (prepared according to example 1) 5.8 ml containing initially 0.90 g (0.80 mmol) of pinoprenol (1) are separated and evaporated to dryness in vacuum. The residue is dissolved in 10 ml of dichloromethane and 20 ml of methanol, 20 ml of 5% aqueous solution of NH$_4$Cl are added, the mixture is agitated, and organic solvents are distilled off in vacuum. After cooling to the room temperature and reaching total transparency of aqueous phase, the latter is removed. The waxy product is dissolved in 10 ml of dichloromethane, 20 ml of methanol are added under agitation followed by the adding 20 ml of 5% aqueous solution of $NH_4Cl$, and organic solvents are distilled off in vacuum. After cooling to the room temperature and reaching total transparency of aqueous phase, the latter is removed. The procedure is repeated 2 times. The residue is washed with 3 ml of distilled water and 3 ml of methanol and dissolved in 5 ml of pentane. 25 ml of acetone are added to the solution, the mixture is agitated, and pentane is evaporated off. After reaching total transparency of supernatant, it is removed. The residue is dissolved in 5 ml of pentane, and the procedure is repeated. The waxy substance is dried in vacuum at 50-60° C. and 0.88 g (0.72 mmol) of ammonium pinoprenyl hydrogen phosphate (8) is obtained; the yield is 90%.

$^1H$ NMR ($CDCl_3$—$CD_3OD$, 5:1): 5.30 (1H, t, J 7.0, HC2=), 5.05 (15H, m, CH=), 4.30 (2H, dd, $J_{H,H}=J_{H,P}=6.0$, $CH_2O$—), 1.95 (60H, m, $CH_2$—), 1.68 (3H, s, $CH_3$—C3=), 1.60 (39H, m, $CH_3C=$, Z- and $W_Z$-isoprene unit), 1.51 (9H, m, $CH_3C=$, E- and $W_E$-isoprene unit). $^{31}P$ NMR ($CDCl_3$—$CD_3OD$, 5:1): 1.8 (0.96 P, s, pinoprenyl phosphate), −6.1 (0.02 P, br.d, $P_\beta$, pinoprenyl diphosphate), −7.9 (0.02 P, br.d, $P_\beta$, pinoprenyl diphosphate).

Example 9

Preparation of Dimethyl Hydroxyethyl Ammonium Pinoprenyl Hydrogen Phosphate (9)

From the final reaction mixture (prepared according to example 1) 1.47 ml containing initially 0.22 g (0.20 mmol) of pinoprenol (1) is separated and evaporated to dryness in vacuum. The residue is dissolved in 3.0 ml ethanol, 4 ml of 2.5% aqueous solution of dimethyl hydroxyethyl ammonium chloride is added, the mixture is agitated, and ethanol is distilled off in vacuum. After cooling to the room temperature and reaching total transparency of aqueous phase, the latter is removed. The waxy product is dissolved in 2.0 ml of dichloromethane, 3.0 ml of ethanol are added under agitation followed by the adding 4 ml of 2.5% aqueous solution of dimethyl hydroxyethyl ammonium chloride, the mixture is agitated, and organic solvents are distilled off in vacuum. After cooling to the room temperature and reaching total transparency of aqueous phase, the latter is removed. The residue is washed with 2.0 ml of distilled water and 2.0 ml of ethanol and dissolved in 1 ml of diethyl ether. 10 ml of acetone are added to the solution, the mixture is agitated, and diethyl ether is evaporated off. After reaching total transparency of supernatant, it is removed. The residue is dissolved in 1.0 ml of diethyl ether, and the procedure is repeated. The waxy substance is dried in vacuum at 50-60° C. and 0.23 g (0.18 mmol) of dimethyl hydroxyethyl ammonium pinoprenyl hydrogen phosphate (9) is obtained; the yield is 90%.

$^1H$ NMR ($CDCl_3$—$CD_3OD$, 5:1): 5.29 (1H, t, J 7.0, HC2=), 5.04 (15H, m, CH=), 4.32 (2H, dd, $J_{H,H}=J_{H,P}=6.0$, $CH_2O$—), 3.90 (6H, s, $CH_3N$—), 3.25 (2H, m, $CH_2N$—), 1.92 (60H, m, $CH_2$—), 1.68 (3H, s, $CH_3$—C3=), 1.60 (39H, m, $CH_3C=$, Z- and $W_Z$-isoprene unit), 1.51 (9H, m, $CH_3C=$, E- and $W_E$-isoprene unit). $^{31}P$ NMR ($CDCl_3$—$CD_3OD$, 5:1): 1.3 (0.95 P, s, pinoprenyl phosphate), −8.6 (0.025 P, br.d, $P_\alpha$, pinoprenyl diphosphate), −9.4 (0.025 P, br.d, $P_\beta$, pinoprenyl diphosphate).

Example 10

Preparation of Sodium 2,3-dihydropinoprenyl Hydrogen Phosphate (10)

The final reaction mixture prepared according to example 2 is evaporated to dryness in vacuum. The residue is dissolved in 1.0 ml of isopropanol, 5.0 ml of 5% aqueous solution of NaCl are added, the mixture is agitated, and isopropanol is distilled off in vacuum. After cooling to the room temperature and reaching total transparency of aqueous phase, the latter is removed. The waxy product is dissolved in 1.0 ml of dichloromethane, 1.0 ml of isopropanol is added at agitation followed by the adding 5.0 ml of 5% aqueous solution of NaCl, and organic solvents are distilled off in vacuum. After cooling to the room temperature and reaching total transparency of aqueous phase, the latter is removed. The procedure is repeated 2 times. The residue is washed with 1.0 ml of distilled water and 1.0 ml of isopropanol and dissolved in 0.50 ml of dichloromethane. 5.0 ml of acetone are added to the solution, the mixture is agitated, and dichloromethane is evaporated off. After reaching total transparency of supernatant, it is removed. The residue is dissolved in 0.50 ml of dichloromethane, and the procedure is repeated. The waxy substance is dried in vacuum at 50-60° C. and 0.100 g (0.083 mmol) of sodium 2,3-dihydropinoprenyl hydrogen phosphate (10) is obtained; the yield is 83%.

$^1H$ NMR ($CDCl_3$—$CD_3OD$, 5:1): 5.00 (15H, m, CH=), 3.95 (2H, m, $CH_2O$—), 1.97 (58H, m, $CH_2$—), 1.60 (39H, m, $CH_3C=$, Z- and $W_Z$-isoprene unit), 1.53 (9H, m, $CH_3C=$, E- and $W_E$-isoprene unit), 1.37-1.04 (5H, m, CH—C3, $CH_2$—C2 and $CH_2$—C4), 0.83 (3H, d, $J_{H,H}$ 6.0, $CH_3$—C3). $^{31}P$ NMR ($CDCl_3$—$CD_3OD$, 5:1): 4.3 (s).

Example 11

Preparation of Sodium Moraprenyl Hydrogen Phosphate (11)

From the final reaction mixture (prepared according to example 3) 153 ml containing initially 15.3 g (20 mmol) of moraprenol (3) are separated and evaporated to dryness in vacuum. The residue is dissolved in 200 ml of ethanol, 200 ml of 5% aqueous solution of NaCl are added, the mixture is agitated, and ethanol is distilled off in vacuum. After cooling to the room temperature and reaching total transparency of aqueous phase, the latter is removed. The waxy product is dissolved in 100 ml of dichloromethane, 200 ml of ethanol are added under agitation followed by the adding 200 ml of 5% aqueous solution of NaCl, and organic solvents are distilled off in vacuum. After cooling to the room temperature and reaching total transparency of aqueous phase, the latter is removed. The procedure is repeated 2 times. The residue is washed with 20 ml of distilled water and 20 ml of ethanol and dissolved in 100 ml of dichloromethane. 250 ml of acetone are added to the solution, the mixture is agitated, and dichloromethane is evaporated off. After reaching total transparency of supernatant, it is removed. The residue is dissolved in 100 ml of dichloromethane, and the procedure is repeated. The waxy substance is dried in vacuum at 50-60° C. and 15.1 g (17.4 mmol) of sodium moraprenyl hydrogen phosphate (11) is obtained; the yield is 87%.

$^1H$ NMR ($CDCl_3$—$CD_3OD$, 5:1): 5.30 (1H, t, J 7.0, HC2=), 5.05 (10H, m, CH=), 4.30 (2H, br. dd, $J_{H,H}=J_{H,P}=6.0$, $CH_2O$—), 1.95 (40H, m, $CH_2$—), 1.68 (3H, s, $CH_3$—C3=), 1.60 (21H, m, $CH_3C=$, Z- and $W_Z$-isoprene unit), 1.53 (12H, m, $CH_3C=$, E- and $W_E$-isoprene unit). $^{31}P$ NMR ($CDCl_3$—$CD_3OD$, 5:1): 4.1 (s).

Example 12

Preparation of Ammonium Moraprenyl Hydrogen Phosphate (12)

From the final reaction mixture (prepared according to example 3) 153 ml containing initially 15.3 g (20 mmol) of moraprenol (3) are separated and evaporated to dryness in vacuum. The residue is dissolved in 200 ml of ethanol, 200 ml of 5% aqueous solution of NH$_4$Cl areded, the mixture is agitated, and ethanol is distilled off in vacuum. After cooling to the room temperature and reaching total transparency of aqueous phase, the latter is removed. The waxy product is dissolved in 100 ml of dichloromethane, 200 ml of ethanol are added under agitation followed by the adding 200 ml of 5% aqueous solution of NH$_4$Cl, and organic solvents are distilled off in vacuum. After cooling to the room temperature and reaching total transparency of aqueous phase, the latter is removed. The procedure is repeated 2 times. The residue is washed with 20 ml of distilled water and 20 ml of ethanol and dissolved in 100 ml of dichloromethane. 250 ml of acetone are added to the solution, the mixture is agitated, and dichloromethane is evaporated off. After reaching total transparency of supernatant, it is removed. The residue is dissolved in 100 ml of dichloromethane, and the procedure is repeated. The waxy substance is dried in vacuum at 50-60° C. and 15.1 g (17.4 mmol) of ammonium moraprenyl hydrogen phosphate (12) is obtained; the yield is 87%.

$^1$H NMR (CDCl$_3$—CD$_3$OD, 5:1): 5.30 (1H, t, J 7.0, HC2=), 5.05 (10H, m, CH=), 4.30 (2H, dd, J$_{H,H}$=J$_{H,P}$=6.0, CH$_2$O—), 1.95 (40H, m, CH$_2$—), 1.68 (3H, s, CH$_3$—C3=), 1.60 (21H, m, CH$_3$C=, Z- and W$_Z$-isoprene unit), 1.52 (12H, m, CH$_3$C=, E- and W$_E$-isoprene unit). $^{31}$P NMR (CDCl$_3$—CD$_3$OD, 5:1): 1.6 (0.95 P, s, moraprenyl phosphate), −6.2 (0.025 P, br.d, P$_\alpha$, moraprenyl diphosphate), −7.8 (0.025 P, br.d, P$_\beta$, moraprenyl diphosphate).

Example 13

Preparation of Magnesium Moraprenyl Phosphate (13)

From the final reaction mixture (prepared according to example 3) 15.3 ml containing initially 1.53 g (2.0 mmol) of moraprenol (3) are separated and evaporated to dryness in vacuum. The residue is dissolved in 20 ml of ethanol, 20 ml of 2.5% aqueous solution of MgSO$_4$ are added, the mixture is agitated, and ethanol is distilled off in vacuum. After cooling to the room temperature and reaching total transparency of aqueous phase, the latter is removed. The waxy product is dissolved in 10 ml of dichloromethane, 20 ml of ethanol are added under agitation followed by the adding 20 ml of 5% aqueous solution of MgSO$_4$, and organic solvents are distilled off in vacuum. After cooling to the room temperature and reaching total transparency of aqueous phase, the latter is removed. The residue is washed with 5.0 ml of distilled water and 5.0 ml of ethanol and dissolved in 5.0 ml of dichloromethane. 25 ml of acetone are added to the solution, the mixture is agitated, and dichloromethane is evaporated off. After reaching total transparency of supernatant, it is removed. The residue is dissolved in 5.0 ml of dichloromethane, and the procedure is repeated. The waxy substance is dried in vacuum at 50-60° C. and 1.56 g (1.80 mmol) of ammonium moraprenyl hydrogen phosphate (13) is obtained; the yield is 90%.

$^1$H NMR (CDCl$_3$—CD$_3$OD, 5:1): 5.14 (10H, m, CH=), 2.12 (38H, m, CH$_2$—), 1.70 (21H, m, CH$_3$C=, Z- and W$_Z$-isoprene unit), 1.61 (12H, m, CH$_3$C=, E- and W$_E$-isoprene unit). $^{31}$P NMR (CDCl$_3$—CD$_3$OD, 5:1): 1.3 (very br. very low intensity singlet).

Example 14

Preparation of Sodium Betulaprenyl Hydrogen Phosphate (14)

From the final reaction mixture (prepared according to example 4) 30 ml containing initially 2.65 g (5.3 mmol) of betulaprenol (4) are separated and evaporated to dryness in vacuum. The residue is dissolved in 20 ml of methanol, 40 ml of 5% aqueous solution of NaCl is added, the mixture is agitated, and methanol is distilled off in vacuum. After cooling to the room temperature and reaching total transparency of aqueous phase, the latter is removed. The waxy product is dissolved in 20 ml of diethyl ether, 20 ml of methanol are added under agitation followed by the adding 40 ml of 5% aqueous solution of NaCl, and organic solvents are distilled off in vacuum. After cooling to the room temperature and reaching total transparency of aqueous phase, the latter is removed. The procedure is repeated 2 times. The residue is washed with 10 ml of distilled water and 10 ml of methanol and dissolved in 20 ml of diethyl ether. 50 ml of acetone are added to the solution, the mixture is agitated, and diethyl ether is evaporated off. After reaching total transparency of supernatant, it is removed. The residue is dissolved in 20 ml of diethyl ether, and the procedure is repeated. The waxy substance is dried in vacuum at 50-60° C. and 2.71 g (4.5 mmol) of sodium betulaprenyl hydrogen phosphate (14) is obtained; the yield is 85%.

$^1$H NMR (CDCl$_3$—CD$_3$OD, 5:1): 5.31 (1H, t, J 7.0, HC2=), 5.04 (6H, m, CH=), 4.28 (2H, br. dd, J$_{H,H}$=J$_{H,P}$=6.0, CH$_2$O—), 2.02 (24H, m, CH$_2$—), 1.67 (3H, s, CH$_3$—C3=), 1.59 (12H, m, CH$_3$C=, Z- and W$_Z$-isoprene unit), 1.51 (9H, m, CH$_3$C=, E- and W$_E$-isoprene unit). $^{31}$P NMR (CDCl$_3$—CD$_3$OD, 5:1): 4.3 (s).

Example 15

Preparation of Ammonium Betulaprenyl Hydrogen Phosphate (15)

From the final reaction mixture (prepared according to example 4) 30 ml containing initially 2.65 g (5.3 mmol) of betulaprenol (4) are separated and evaporated to dryness in vacuum. The residue is dissolved in 20 ml of ethanol, 40 ml of 5% aqueous solution of NH$_4$Cl are added, the mixture is agitated, and ethanol is distilled off in vacuum. After cooling to the room temperature and reaching total transparency of aqueous phase, the latter is removed. The waxy product is dissolved in 20 ml of dichloromethane, 20 ml of ethanol are added under agitation followed by the adding 40 ml of 5% aqueous solution of NH$_4$Cl, and organic solvents are distilled off in vacuum. After cooling to the room temperature and reaching total transparency of aqueous phase, the latter is removed. The procedure is repeated 2 times. The residue is washed with 10 ml of distilled water and 10 ml of ethanol and dissolved in 20 ml of dichloromethane. 50 ml of acetone are added to the solution, the mixture is agitated, and dichloromethane is evaporated off. After reaching total transparency of supernatant, it is removed. The residue is dissolved in 20 ml of dichloromethane, and the procedure is repeated. The waxy substance is dried in vacuum at 50-60° C. and 2.90 g (4.8 mmol) of ammomium betulaprenyl hydrogen phosphate (15) is obtained; the yield is 90%.

$^1$H NMR (CDCl$_3$—CD$_3$OD, 5:1): 5.31 (1H, t, J 7.0, HC2=), 5.04 (6H, m, CH=), 4.28 (2H, dd, J$_{H,H}$=J$_{H,P}$=6.0, CH$_2$O—), 2.02 (24H, m, CH$_2$—), 1.67 (3H, s, CH$_3$—C3=), 1.61 (12H, m, CH$_3$C=, Z- and W$_Z$-isoprene unit), 1.52 (9H, m, CH$_3$C=, E- and W$_E$-isoprene unit). $^{31}$P NMR (CDCl$_3$—CD$_3$OD, 5:1): 1.8 (0.96 P, s, betulaprenyl phosphate), −6.1 (0.02 P, br.d, P$_\alpha$, betulaprenyl diphosphate), −7.9 (0.02 P, br.d, P$_\beta$, betulaprenyl diphosphate).

Example 16

(Comparative with the Closest Analog Method).
Preparation of Moraprenyl Phosphate Moraprenol (α-unsaturated C55-polyprenol from mulberry leaves, 100 mg, 0.13 mmol) is dissolved in 0.5 ml (5 mmol) of trichloroacetonitrile and 1.2 ml of solution of mono (tetra-n-butylammonium)-phosphate (0.54 mmol) in abs. acetonitrile is added with shaking. After 10 min the solvents are distilled off in vacuum, the residue is dissolved in 1 ml of toluene, and the solvent is evaporated off; the procedure is repeated. The residue is dissolved in 1.5 ml of tetrahydrofuran, and 0.3 ml of 25% ammonia is added. After 10-15 min 5 ml of toluene and 5 ml of methanol are added, and the mixture is agitated. After settling, the supernatant is separated, and the precipitate is washed 2 times with the mixture toluene-methanol, 1:1. The solution and washing liquids are evaporated to dryness and 2 times with 3 ml of propanol for toluene removing, the residue is dissolved in 1 ml of propanol, and 40 ml of distilled water are added gradually with shaking. 30 mg (0.265 mmol) of 4-dimethylaminopyridine are added to the solution, and the mixture is boiled during 8 h with reflux condenser. After cooling, 60 ml of propanol is added and evaporated to dryness at rotatory evaporator. The residue is dissolved in 30 ml of the mixture chloroform-methanol, 2:1 and agitated during 1 h with excess of Dowex 50×8(Py$^+$). The resin is filtered off, washed with the same solvent mixture, 0.5 ml of 25% ammonia is added, and the solution is evaporated to dryness. The residue is dissolved in toluene, and after 3 h at 4° C. the residue is removed. The toluene solution is evaporated, the residue is dissolved in 50 ml of the mixture chloroform-methanol, 2:1 and applied on the column (1×10 cm) with DEAE-cellulose DE-52 equilibrated with the same solvent mixture. The column is washed with 30 ml of the mixture, 30 ml of methanol and the desired product is eluted with 50 ml of 40 mM solution of ammonium acetate in methanol. The product is homogeneous by TLC in the system chloroform-methanol-water, 60:25:4, the ratio of acid-labile phosphate and polyprenol is 1.05:1 (theoretically 1:1). The yield is 0.11 mmol (85%).

So it is obvious from the above that the present method for producing polyprenyl phosphates is significantly more simple, manufacturable and profit-proved than the closest analog. The method can be applied both in micro- and macroscales necessary for developing and producing a new generation of pharmaceuticals containing a number of the physiologically and therapeutically accepted salts of the mentioned compounds as active ingredients.

The invention claimed is:

1. A method for producing polyprenyl phosphates having general structural formula (I):

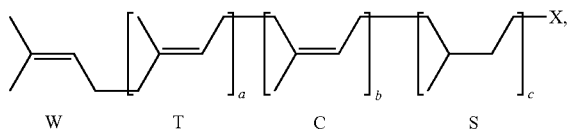

where each isoprene unit contains 5 carbon atoms, W is an ω-end isoprene unit, T is a trans-isoprene unit, C is a cis-isoprene unit, S is a 2,3-dihydroisoprene unit, a=0-10, b=0-39, c=0-1, a+b+c=4-40, and X is a group having the general formula OPO$_3$MM', wherein M and M' are identical or different and are selected from the group consisting of a hydrogen cation, a monovalent inorganic cation, a monovalent organic cation, a divalent inorganic cation, and a divalent organic cation, the method comprising the steps of:

carrying out a phosphorylation reaction of the corresponding polyprenol or the mixture of oligomer homologues of general formula (I), where X is a hydroxyl group, using the substituted ammonium salt of phosphoric acid in the presence of condensing agent in a medium consisting of a first aprotic organic solvent; and isolating, by extraction and precipitation, the polyprenyl phosphate in the form of disubstituted salts thereof with monovalent cations, wherein the polyprenyl phosphate is isolated in the form of disubstituted salt thereof with monovalent cation when carrying out steps of:

distilling off the first aprotic organic solvent from the reaction mixture or from its part;

removing the water-soluble impurities from the obtained residue by extraction in the system the first organic solvent-water;

evaporating the organic phase;

precipitating the unpurified disubstituted salt of polyprenyl phosphate by treating with a solution of the monovalent metal salt and hydroxide of this metal in the alcohol;

extracting non-phosphorylated compounds consecutively with the alcohol and second aprotic organic solvent in which the polyprenyl phosphate salt is insoluble; and obtaining the disubstituted salt of polyprenyl phosphate having at least 95 wt % purity.

2. The method according to claim 1, wherein polyprenol molecules contain at least 6 isoprene units.

3. The method according to claim 2, wherein polyprenol molecules contain from 6 to 20 isoprene units.

4. The method according to claim 1, wherein the substituted ammonium salt of phosphoric acid is selected from the group consisting of bis(diisopropylethylammonium) hydrogen phosphate and a dihydrophosphate selected from the group consisting of diisopropylethylammonium dihydrophosphate, tetramethylammonium dihydrogen phosphate, tetraethylammonium dihydrogen phosphate, tetrabutylammonium dihydrogen phosphate and cetyltrimethylammonium dihydrogen phosphate.

5. The method according to claim 4, wherein tetrabutylammonium dihydrogen phosphate is used as the substituted ammonium salt of phosphoric acid.

6. The method according to claim 4, wherein the condensing agent is selected from the group consisting of trichloroacetonitrile and dicyclohexylcarbodiimide.

7. The method according to claim 6, wherein the molar ratio of polyprenol, the substituted ammonium salt of phosphoric acid and trichloroacetonitrile is within 1:0.1-10:0.1-10.

8. The method according to claim 6, wherein the mentioned molar ratio of polyprenol, the substituted ammonium salt of phosphoric acid and trichloroacetonitrile is approximately 1:1:1.

9. The method according to claim 1, wherein the first aprotic organic solvent is selected from the group consisting of benzene, toluene, dichloromethane, chloroform, dimethylformamide, a mixture of benzene and acetonitrile, a mixture of toluene and acetonitrile, a mixture of dichloromethane and acetonitrile, a mixture of chloroform and acetonitrile, and a mixture of dimethylformamide and acetonitrile.

10. The method according to claim 1, wherein the first organic solvent in the system organic solvent-water is selected from the group consisting of petroleum ether, benzene, toluene, chloroform, dichloromethane, butanol, isoamyl alcohol and a mixture thereof.

11. The method according to claim 1, wherein the alcohol is selected from the group consisting of methanol, ethanol, propanol, isopropanol and a mixture thereof.

12. The method according to claim 1, wherein the solution is a solution containing from 1 to 10 wt % of a compound selected from the group consisting of lithium formate, sodium formate, potassium formate, acetate, chloride, bromide, iodide, and from 0 to 10 wt % of corresponding metal hydroxide, in the alcohol.

13. The method according to claim 1, wherein the second aprotic organic solvent is selected from the group consisting of acetonitrile, acetone and a mixture thereof.

14. A method for producing polyprenyl phosphates having general structural formula (I):

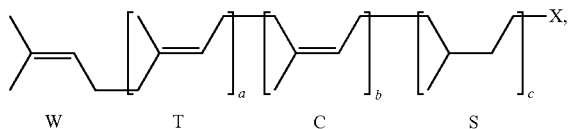

where each isoprene unit contains 5 carbon atoms, W is an ω-end isoprene unit, T is a trans-isoprene unit, C is a cis-isoprene unit, S is a 2,3-dihydroisoprene unit, a=0-10, b=0-39, c=0-1, a+b+c=4-40, and X is a group having the general formula $OPO_3MM'$, wherein M and M' are identical or different and are selected from the group consisting of a hydrogen cation, a monovalent inorganic cation, a monovalent organic cation, a divalent inorganic cation, and a divalent organic cation, the method comprising the steps of:

carrying out a phosphorylation reaction of the corresponding polyprenol or the mixture of oligomer homologues of general formula (I), where X is a hydroxyl group, using the substituted ammonium salt of phosphoric acid in the presence of condensing agent in a medium consisting of a first aprotic organic solvent; and isolating, by extraction and precipitation, the polyprenyl phosphate in the form of monosubstituted salts thereof with monovalent cations or in the form of salts thereof with divalent cations;

wherein the mentioned polyprenyl phosphate is isolated in the form of its monosubstituted salt thereof with monovalent cation or of salt with divalent cation, when carrying out steps of:

distilling off the first aprotic solvent from the reaction mixture or from a part thereof;

removing the water-soluble impurities from the obtained residue by treating its solution in second organic solvent with aqueous solution of the salt of ammonium, mono- or divalent metal or organic base with strong acid followed by evaporating the second organic solvent and removing aqueous phase;

extracting the non-phosphorylated impurities by solubilizing the obtained waxy residue in third organic solvent and adding the second organic solvent in which the salt of polyprenyl phosphate is insoluble, followed by evaporating the third organic solvent and simultaneously precipitating the desired product;

removing a supernatant; and obtaining the monosubstituted salt of polyprenyl phosphate or its salt with divalent cation having at least 95 wt % purity.

15. The method according to claim 14, wherein the second organic solvent is selected from the group consisting of the alcohol, a mixture of alcohol with carbon tetrachloride, a mixture of alcohol with pentane, a mixture of alcohol with hexane, a mixture of alcohol with dichloromethane, a mixture of alcohol with chloroform and a mixture of alcohol with diethyl ether.

16. The method according to claim 14, wherein a compound selected from the group consisting of methanol, ethanol, propanol or isopropanol is used as the alcohol.

17. The method according to claim 14, wherein an aqueous solution containing from 0.5 to 10 wt % of compound selected from the group consisting of nitrate, bromide, chloride, sulfate or hydrogen sulfate of lithium, sodium, potassium, ammonium, hydroxyethylammonium, dimethyl hydroxyethyl ammonium, choline, triethylammonium or triethanolammonium as monovalent cation, or calcium, magnesium, manganese or zinc as divalent cation is used as the aqueous solution of the salt.

18. The method according to claim 14, wherein the third organic solvent is selected from the group consisting of diethyl ether, dichloromethane, pentane, hexane and a mixture thereof.

19. The method according to claim 14, wherein the second aprotic organic solvent is selected from the group consisting of acetonitrile, acetone and a mixture thereof.

* * * * *